US012588941B2

(12) United States Patent

Mueller et al.

(10) Patent No.: US 12,588,941 B2

(45) Date of Patent: Mar. 31, 2026

(54) ELECTROSURGICAL INSTRUMENT

(71) Applicant: Erbe Elektromedizin GmbH,
Tuebingen (DE)

(72) Inventors: Marc Mueller, Nagold (DE); **Achim
Brodbeck, Metzingen (DE); Frederik
Kleber**, Wannweil (DE)

(73) Assignee: Erbe Elektromedizin GmbH,
Tuebingen (DE)

( * ) Notice: Subject to any disclaimer, the term of this
patent is extended or adjusted under 35
U.S.C. 154(b) by 570 days.

(21) Appl. No.: 18/076,056

(22) Filed: Dec. 6, 2022

(65) Prior Publication Data

US 2023/0190359 A1    Jun. 22, 2023

(30) Foreign Application Priority Data

Dec. 17, 2021    (EP) .................................... 21215672

(51) Int. Cl.
    *A61B 18/14*        (2006.01)
    *A61B 18/00*        (2006.01)

(52) U.S. Cl.
    CPC .... *A61B 18/14* (2013.01); *A61B 2018/00029*
    (2013.01); *A61B 2018/00982* (2013.01); *A61B
    2218/007* (2013.01)

(58) Field of Classification Search
    CPC .......... A61B 18/14; A61B 2018/00029; A61B
    2018/00184; A61B 2018/00202; A61B
    2018/0097; A61B 2018/00982; A61B
    2018/1412; A61B 2018/1425; A61B
    2218/002; A61B 2218/007

USPC ...................................................... 606/45–46
See application file for complete search history.

(56) References Cited

U.S. PATENT DOCUMENTS

| | | | |
|---|---|---|---|
| 5,197,963 A * | 3/1993 | Parins ..................... | A61M 1/84 |
| | | | 606/41 |
| 5,456,681 A | 10/1995 | Hajjar | |
| 5,861,002 A * | 1/1999 | Desai ..................... | A61M 1/774 |
| | | | 606/139 |
| 6,126,653 A | 10/2000 | Hajjar | |
| 7,303,561 B2 * | 12/2007 | Ouchi ................ | A61B 1/00101 |
| | | | 606/45 |
| 10,154,786 B2 | 12/2018 | Fischer et al. | |
| 10,251,695 B2 | 4/2019 | Fischer et al. | |
| 10,695,120 B2 | 6/2020 | Hagg | |
| 2019/0231416 A1 * | 8/2019 | Hsu ..................... | A61B 18/149 |

FOREIGN PATENT DOCUMENTS

| | | |
|---|---|---|
| CN | 103124532 A | 5/2013 |
| EP | 1 210 904 A2 | 6/2002 |
| EP | 2 659 846 A1 | 11/2013 |
| EP | 2 815 695 A1 | 12/2014 |
| EP | 2 815 713 B1 | 8/2015 |
| EP | 2 862 533 B1 | 9/2019 |

(Continued)

*Primary Examiner* — Michael F Peffley
(74) *Attorney, Agent, or Firm* — Blank Rome LLP

(57) ABSTRACT

Instruments having a hood that defines and surrounds a flow chamber. The flow chamber can serve for suction of emissions that are produced due to influence of an electrode supplied with high frequency voltage on biological tissue. For elimination of tissue deposition and other clogging from the flow chamber the electrode is surrounded by a movable hood that can be transitioned for cleaning purposes out of its operating position into a cleaning position.

15 Claims, 3 Drawing Sheets

(56)        References Cited

FOREIGN PATENT DOCUMENTS

| | | | |
|---|---|---|---|
| JP | 2010125273 | A | 6/2010 |
| WO | WO 2016/138008 | A1 | 9/2016 |
| WO | WO 2016/177600 | A1 | 11/2016 |
| WO | WO 2019/152377 | A1 | 8/2019 |

* cited by examiner

ELECTROSURGICAL INSTRUMENT

CROSS-REFERENCE TO RELATED APPLICATION

This application claims priority to European Patent Application No. 21215672.3, filed Dec. 17, 2021, the entirety of which is incorporated by reference herein.

TECHNICAL FIELD

The invention refers to an electrosurgical instrument for treatment of human or animal patients. Particularly, the invention refers to such an instrument that comprises an optical element for light receipt or light emission in addition to an electrode provided for surgical treatment of tissue.

BACKGROUND

An electrosurgical instrument having an electrode is known from EP 2 659 846 A1 that influences biological tissue by means of an electrical current. In addition, one or more light receipt devices are provided on the instrument that receive light originating from a spark created at the electrode. This light is provided to a light analysis device in order to determine tissue features therefrom.

A similar instrument is known from EP 2 815 695 A1. Light emitting from a respective spark has to be captured by the optical elements of the instrument as undistorted as possible. A deposition, tissue fragments or the like that are present on the optical elements distort this.

In this regard EP 2 815 713 B1 proposes the location of a light receiving optical fiber in an interior fluid channel of the instrument. It comprises fluid exit openings via which light can enter into the fluid channel. In the vicinity of the light fluid exit openings an electrode is provided serving for tissue treatment.

In addition, an instrument having an optical fiber that is axially movable inside a tube is known from U.S. Pat. No. 6,126,653 A. A brush set is arranged at the distal end of the tube. During forwarding the optical fiber in distal direction, the optical fiber brushes through the brushes. During retraction of the optical fiber the brushes wipe off particles deposited on the optical fiber.

A similar concept having a movable optical fiber is pursued by WO 2016/177600 A1. The instrument comprises cleaning brushes that touch an optical fiber that is axially movable at its circumference.

On the contrary, EP 1 210 904 A2 provides an instrument having an outer tube and an optical fiber that is axially movably supported therein. At the distal end the outer tube comprises a pivotable cap having a cleaning lip. If the optical fiber is axially forwarded in distal direction, it pivots the end cap to the side due to its movement. Concurrently the cleaning lip brushes over the face side end of the optical fiber and thus cleans it.

EP 2 862 533 B1 discloses an electrosurgical instrument having a suction device. It comprises a fluid channel with an end side hood surrounding the suction opening. The hood can be immovably connected with the electrode and can be removably arranged on the instrument.

SUMMARY

In practice it cannot always be avoided that elements provided for cleaning of light passage windows, such as brushes or the like, are themselves contaminated.

It is the object of the invention to provide a electrosurgical instruments having optical elements that can be maintained operative for a long time.

Embodiments of the invention include instruments for open surgical use, an instrument provided for the laparoscopic use, a probe that is to be used in an endoscopic manner or the like. In any case, the instrument comprises an instrument body at the distal end of which an electrode is provided for treatment of biological tissue. Alternatively, the electrode can be provided on an element connected with the instrument body. Such an element can be connected with the instrument body, e.g. in a latched manner. For example, the electrode is supplied with high frequency electrical current and acts on the tissue under production of an electrical spark.

At least one fluid channel is provided in the instrument body or in an element that can be connected therewith, the fluid channel having an opening at the distal end of the body or the element. This opening can particularly serve for suction of gases, vapors, fumes, tissue particles or the like produced at the operation location. Such an element comprising the suction channel can also comprise the electrode or an optical element that captures light originating from the electrode and providing it to a light analysis device. The optical element can also serve to conduct light to the operation location.

A hood arranged on the instrument body or an element connected with the instrument body thereby limits a chamber into which and/or through which the electrode extends and inside which the opening of the channel is arranged. The chamber surrounding the electrode channels emissions emitted by the electrode from the operation location and guides them into the fluid channel. This flow guide function is achieved in that the hood projects over the distal face of the instrument body or the element and in this manner forms the mentioned chamber.

In addition, the instrument comprises an optical element that is arranged at the distal end of the instrument body or the element that can be connected therewith at a light passage window. The light passage window can be an opening through which a cone of view of the optical element extends. The light passage window can also be defined by the distal end face of the optical element itself.

During operation—particularly by suction of gases, vapors, fumes and/or tissue particles created at the operation location into the chamber surrounded by the hood—depositions can be created, particularly in front of the light passage window, e.g. in the form of tissue particle accumulations. Such depositions can impede the light passage through the light passage window and so limit the functionality of the instrument.

In the instrument according to the invention the hood is movably arranged on the instrument body or the element attached thereon, so that in a first position it limits the desired, required space for suction of emissions from the operation location and in a second position uncovers the light passage window. In the first position the hood projects beyond the light passage window in distal direction and in this manner blocks a lateral access to the light passage window. Under "lateral access" an access transverse to the longitudinal direction extending from proximal to distal is meant. In the second position the hood does not extend or extends only so little beyond the light passage window in distal direction that the lateral access to the light passage window is unblocked. In this manner the instrument can be cleaned in a simple manner. For this purpose the hood is only transferred from its first into its second position. Particles that are present can be simply removed, e.g. by a cloth.

Thereby it is also avoided that possible particles and other depositions are only smeared or displaced. The handling is easy and intuitive.

As mentioned above, the fluid channel is preferably a suction channel. For this purpose the instrument can be provided with a connection device at its proximal end so that the fluid channel can be connected to a suction device. At least as an option, this channel or another (second) fluid channel can be used as flushing fluid channel. If this is the case, the second channel can be connectable at the proximal end of the instrument or at a connection line of the instrument with a flushing fluid source via a respective connection device. The flushing fluid can be a gaseous fluid, such as air, carbon dioxide, argon, nitrogen or any other gas. The flushing fluid can also be a liquid, such as an aqueous NaCl solution. The second channel or another channel can also serve to supply gas (e.g. argon) to the electrode, e.g. to produce a plasma.

The opening serving for suction, the electrode and the light passage window are preferably arranged next to each other and further preferably surrounded by the hood. Therefore, the opening serving for suction and the light passage window together can be arranged next to each other inside or at the space through which the electrode passes. Thereby the electrode can be arranged projecting in distal direction out of the hood. The hood then limits a distal suction opening by which emissions produced by the electrode during tissue treatment can be sucked and concentrated onto the opening of the fluid channel.

The hood can have a surrounding continuous edge and can be movably arranged in longitudinal direction, i.e. between a distal position and a proximal position. Thereby a translational movement path for the hood can be established. It is, however, also possible to provide a hood is movable along a helical path between a distal first position and a proximal second position. The hood can be configured in a hollow cylindrical or hollow cone-shaped manner. Thus, also the chamber defined by the hood is configured cylindrically or in a truncated cone-shaped manner.

Other configurations can be provided to maintain the hood in the first position and/or the second position. This simplifies the handling. For example, the configuration could include a latching mechanism, clamping mechanism or the like.

In an alternative embodiment the instrument body comprises a bowl-shaped projection and the hood is configured as complementary half bowl. The bowl-shaped projection of the instrument body and the hood are in this case configured to extend only partly around the chamber. In the first position the projection of the instrument and the hood form a ring-shaped surrounding of the chamber, while in its second position the hood is arranged in an overlapping manner with the bowl-shaped projection of the instrument body and thus opens the chamber at least toward one side so that the light passage window is accessible. In so far the instrument body comprises a cleaning window that can be opened or closed by the hood.

BRIEF DESCRIPTION OF THE DRAWINGS

Further details of advantageous embodiments of the invention are subject of the drawing and the respective description. The drawings show.

DETAILED DESCRIPTION

Figure 1:
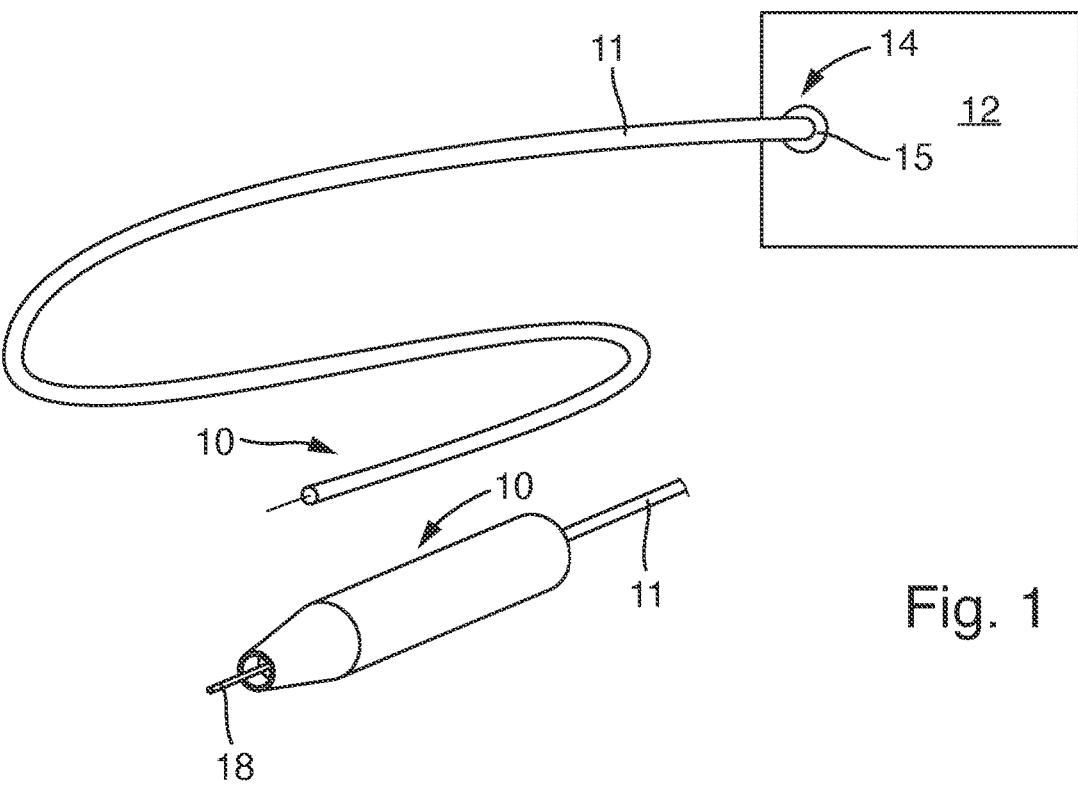
FIG. 1 is an instrument and is an associated apparatus for supply of the instrument in a schematic illustration.

In FIG. 1 an instrument 10 according to the invention is illustrated that is connected to a supplying apparatus 12 by an associated line 11. The instrument 10 can be configured as probe for the endoscopic use, as laparoscopic instrument or as instrument for the open surgical use. Such an instrument 10' for the open surgical use is separately illustrated in FIG. 1. The features and principles explained in the following apply for the instruments 10, 10' similarly independent from their other configuration, particularly independent from whether they are configured for open surgical, laparoscopic or endoscopic use.

Figure 2:
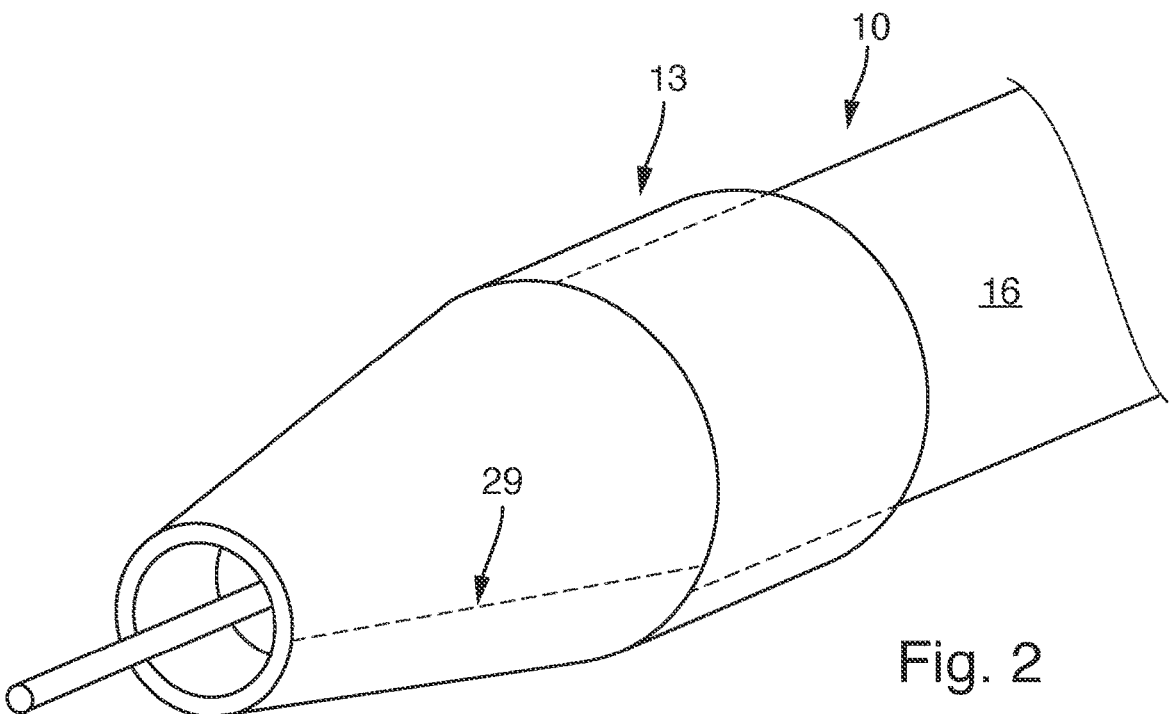
FIG. 2 is the distal end of the instrument of FIG. 1 in a first embodiment and in a schematical perspective illustration.

The instrument 10, 10' comprises a distal end 13 individually illustrated in FIG. 2 and a proximal end 14 that can be provided with an instrument connector 15 by which the instrument 10, 10' is connected with the apparatus 12. The apparatus 12 comprises all elements and units that are necessary to operate instrument 10, 10'.

Part of instrument 10 is an instrument body 16 (FIG. 2, see also FIG. 3) from the distal face 17 of which at least one electrode 18 projects. The electrode can have a needle shape, spatula shape or any other suitable shape for the surgical purpose. For current supply the electrode 18 is connected with apparatus 12 by an electrical conductor 19 extending through the line 11 and by the instrument connector 15. The electrode 18 is supplied by apparatus 12 via conductor 19 with electrical voltage and current, e.g. high frequency current. The voltage is thereby preferably so high that a spark can be produced between electrode 18 and biological tissue located in the surrounding area.

A fluid channel 20 ending in an opening 21 that opens out at the distal face 17 extends through instrument body 16. The fluid channel 20 extends through instrument body 16 and line 11 up to instrument connector 15. In the apparatus 12 a suction device can be provided that continuously or as necessary creates a gas flow in proximal direction and thus a suction effect in the opening 21.

Figure 3:
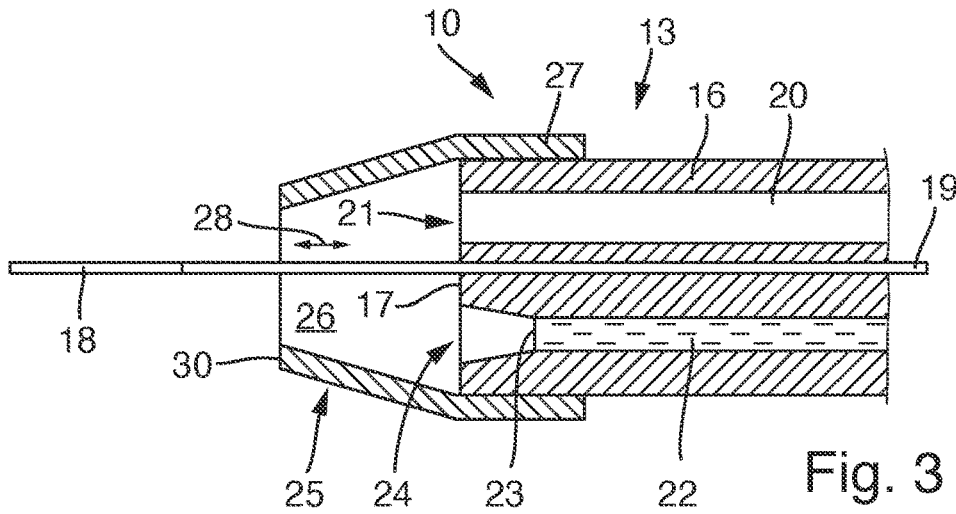
FIG. 3 is the distal end of the instrument of FIG. 2 with its hood in a first position in a longitudinally cut illustration.

Part of the instrument 10 is in addition an optical element 22 that is illustrated in FIG. 3 as optical fiber by way of example. Instead of a single optical fiber, the optical element 22 can however also consist of a bundle of multiple optical fibers and/or comprise additional optical elements, such as lenses, mirrors or the like. The optical element 22 comprises at its distal end a light passage surface 23 that can emit and/or receive light. The optical element 22 is configured, for example, in the form of an optical fiber extending up to the apparatus connector 15, to supply light captured at the light passage surface 23 to the apparatus 12.

The light passage surface 23 can be arranged flush at the distal face 17 of instrument body 16 or, as illustrated in FIG. 3, can be displaced backward relative to this surface. For this purpose a respective opening is formed in the distal face that forms a light passage window 24. If the light passage surface 23 is arranged flush with the distal face 17, the light passage surface 23 itself forms the light passage window 24.

In addition, a hood 25 is arranged at the distal end 13 of instrument 10 that defines a chamber 26 encompassing the distal face 17 of instrument body 16. Electrode 18 extends through this chamber 26. For example, hood 25 comprises a hollow truncated cone shape. In addition, it can have a hollow cylindrical section 27 that is placed on the—for example cylindrical—outer surface of instrument body 16. The hood 25 serves to improve the suction effect and to distribute the suction effect originating from fluid channel 20 around the entire electrode 18.

Figure 4:
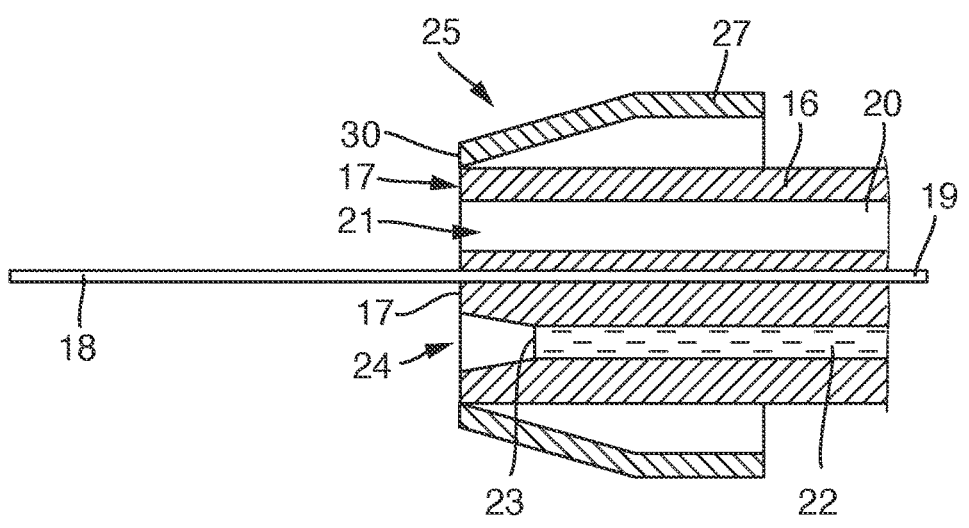
FIG. 4 is the distal end of the instrument according to FIGS. 2 and 3 with its hood in a second position (release position)

The hood 25 is movably arranged between two positions back and forth in axial direction 28. FIG. 3 illustrates the hood 25 in a first position in that the instrument 10 can be used for treatment of tissue and in that the hood 25 has the desired guide effect for the suction flow. FIG. 4 illustrates the hood 25 in its second position axially retracted in proximal direction in which it largely exposes the distal face 17 of instrument body 16. In order to allow such a retraction of hood 25, the hood 25 can comprise a joint 29 illustrated in dashed lines in FIG. 2, e.g. along a surface line, at which the hood 25 can elastically widen, if it is transitioned into the retraction position according to FIG. 4. The spring elastic effect of hood 25 can contribute to keep the hood 25 during use in its first position and to pretension the hood 25 toward this position.

The instrument 10 described so far operates as follows:

For treatment of a patient, instrument 10 or 10' is approached with its electrode 18 to the tissue area to be treated and the generator 12 is activated. The electrode 18 is supplied with high frequency alternating voltage so that a spark is produced between the biological tissue and the electrode 18. Thereby vapor, fume or also tissue fractions and the like, which are produced due to the influence of the spark onto the tissue, are sucked via fluid channel 20. The hood 25 that is in the position illustrated in FIG. 3 thereby distributes the suction effect uniformly around electrode 18 so that a good suction effect is provided.

Via optical element 22 light originating from the spark is captured. It enters via light passage window 24 and light passage surface 23 into optical element 22 and is supplied to the apparatus 12 by the optical element 22. There, an analysis of the received light can be carried out in order to determine features of the tissue, the quality of the spark or other conditions.

Due to the surgical influence on the tissue and the suction effect, it has to be expected that particles, tissue fractions, liquid drops and the like are sucked into chamber 26 and disposed on the light passage window 24. If this is the case, the optical path between the electrode and the light passage window 24 is increasingly blocked.

The instrument 10 according to the invention allows simple cleaning in that the hood 25 is transitioned from its position illustrated in FIG. 3 in a second position illustrated in FIG. 4. While the edge 30 of the hood 25 is located remote in distal direction from the face 17 in the operation position according to FIG. 3 and the hood 25 covers the lateral access to the light passage window 24, the edge 30 is flush or at least near the face 17 in the second position. In this position the light passage window 24 is laterally accessible and can be easily cleaned, e.g. by a cloth, so that the instrument 10 is again ready to operate. In order to establish full operability, the hood 25 is moved back from the position illustrated in FIG. 4 into the position according to FIG. 3.

Latching or clamping mechanisms that are not further illustrated can be provided in order to keep the hood 25 in the operating position according to FIG. 3 and/or the retracted position, i.e. the cleaning position according to FIG. 4.

The description above is assuming that the hood 25 is configured in a hollow truncated cone-shaped manner. However, it is also possible to use other shapes, e.g. a rotation hyperboloid shape, a hollow cylinder shape or the like. In addition, also the joint 29 can be omitted, if hood 25 consists of a sufficiently elastic material or of multiple lamellae that can be spread apart from one another and project from the section 27 in distal direction.

Figure 5:
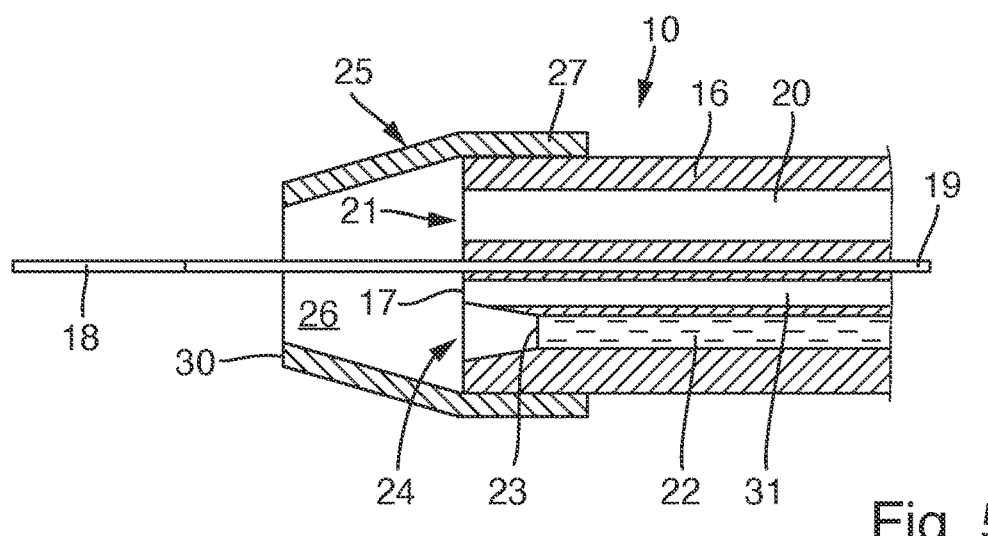
FIG. 5 is a modified embodiment of the instrument according to FIGS. 1 to 3 in a longitudinally cut illustration.

FIG. 5 illustrates another embodiment. For this embodiment the description above applies accordingly without restrictions. It applies moreover that in addition to the fluid channel 20 a second fluid channel 31 can be provided that extends from the instrument connector 15 up to the distal face 17 of instrument body 16. A flushing fluid can be guided via fluid channel 31 to the optical element 22 and particularly its light passage surface 23. The flushing fluid can be a gas or also a liquid, particularly an NACL water solution. The flushing fluid can be supplied by apparatus 12 in order to keep the light passage surface 23 and/or the light passage window 24 clean or to clean it. The supply of flushing fluid can be initiated manually by respective actuation elements or can be carried out automatically, e.g. after the termination of the activation of electrode 18 respectively.

Also in this embodiment of instrument 10 the hood 25 can be displaced between two positions, namely the operating position illustrated in FIG. 5 and a cleaning position according to FIG. 4. The hood 25 is movably arranged in order to allow a lateral access to the light passage window 24 for manual cleaning thereof.

Figure 6:
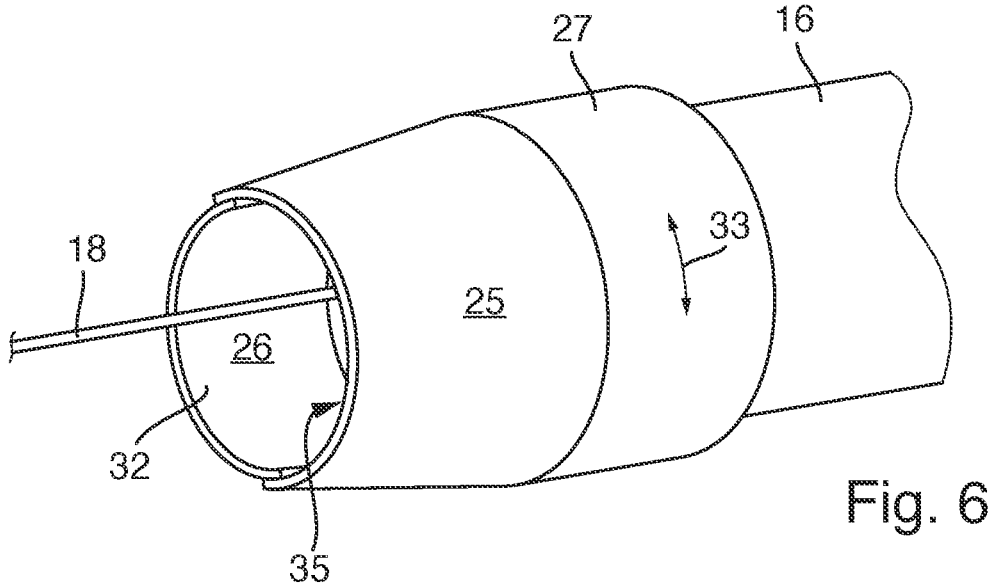
FIG. 6 is another modified embodiment of the instrument with a rotatably supported hood with the hood being in closed position in a schematical perspective illustration.
Figure 7:
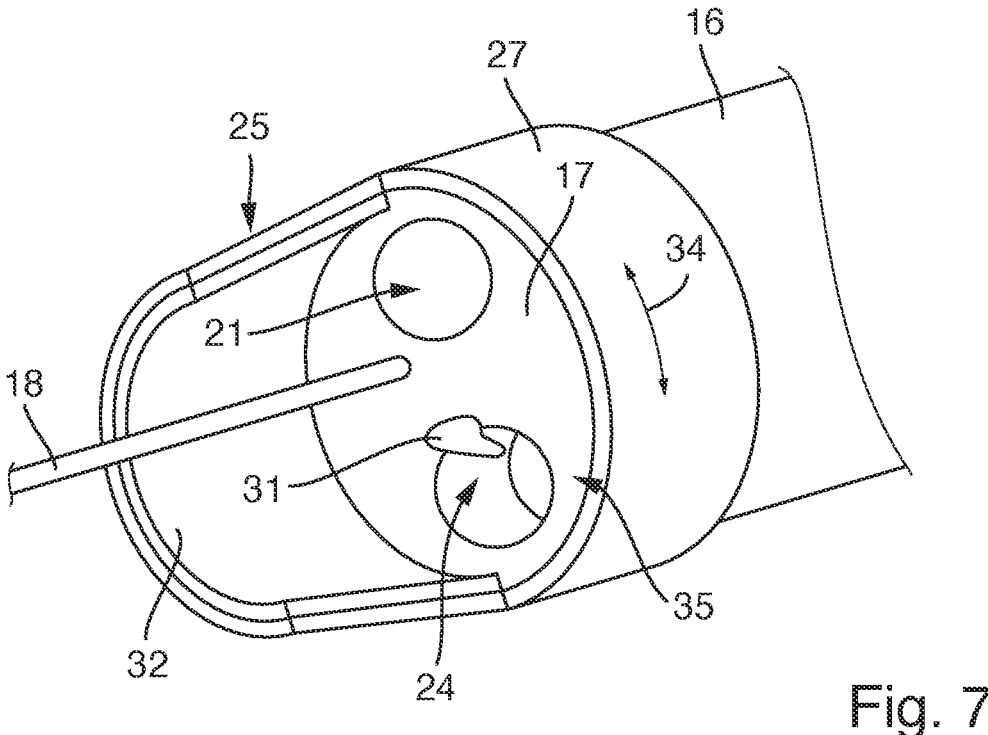
FIG. 7 is the distal end of the instrument according to FIG. 6 with the hood in opening position in a schematical perspective illustration.

The description above requires an axial movement possibility of hood 25. This can be a linear translational movement between two end positions of the hood 25. The path can also be helically wound. FIGS. 6 and 7 show another variation:

In the embodiment of instrument 10 according to FIG. 6, the instrument body 16 comprises a bowl-like extension 32 that defines the chamber 26 approximately around half of its circumference and leaves a cleaning window 35 open at its diametrically opposite side. The other half of the circumference is surrounded by the hood 25 that is here bowl-shaped and that in this manner closes the cleaning window 35. The extension 32 and the hood 25 complement one another to a hollow truncated cone shape, as shown in FIG. 6, and thus commonly surround the chamber 26. According to the description above, instead of the hollow truncated cone shape also any other shape can be selected that channels the suction effect originating from opening 21, as desired around electrode 18.

In the embodiment according to FIGS. 6 and 7, the section 27 of hood 25 is rotatably movably supported on instrument body 16, as indicated by arrows 33, 34. In a first operating position according to FIG. 6, the extension 32 and the hood 25 complement one another to a structure closed around chamber 26. In the second (rotary) position of hood 25 according to FIG. 7, the extension 32 and the hood 25 are approximately congruent so that the cleaning window 35 is open and the distal face 17 of instrument body 16 is at least largely exposed. Particularly the light passage window 24 is accessible unimpededly from the side so that tissue particles or other depositions that have deposited there can be easily removed manually.

The electrode 18 and/or the fluid channel 20 and/or the fluid channel 31 and/or the optical element 22 and/or the hood 25 can be provided, as described, on the instrument body 16 respectively or as an alternative on a separate element that is connected with the instrument body, particularly releasably connected. For example, the element can be connected with the instrument body 16 by a plug connection or a latch connection.

The instrument 10 according to the invention comprises a hood 25 that surrounds a flow chamber 26. It serves for suction of emissions that are produced due to influence of an electrode 18 supplied with high frequency voltage on biological tissue. For elimination of tissue deposition and other clogging from the flow chamber 26 the latter is surrounded by a movable hood 25 that can be transitioned for cleaning purposes out of its operating position into a cleaning position.

The invention claimed is:

1. An instrument for electrosurgical treatment of human or animal patients, comprising:

an instrument body that comprises a distal end and at least one fluid channel that extends from an opening arranged at the distal end in proximal direction through the instrument body, the fluid channel adapted to be connected to a suction device such that a suction is appliable at the opening, an electrode that is held on the distal end of the instrument body, an optical element and a light passage window at a distal end of the optical element, a hood that defines a chamber through which the electrode extends and in which the opening and the light passage window are arranged, wherein the hood is movably supported back and forth between at least a first position in which it covers the light passage window and a second position in which it exposes the light passage window, wherein the electrode is arranged to always protrude distally from the hood in the first position and the second position.

2. The instrument according to claim 1, wherein suction is applied to the at least one fluid channel.

3. The instrument according to claim 1, wherein the electrode can be connected to an electrical generator by a conductor extending through the instrument in proximal direction.

4. The instrument according to claim 1, wherein the opening, the electrode and the light passage window are arranged next to one another at the distal face of the instrument body.

5. The instrument according to claim 1, wherein the electrode is arranged projecting in the distal direction out of the hood.

6. The instrument according to claim 1, wherein the hood comprises a distal suction opening.

7. The instrument according to claim 6, wherein the suction opening comprises a continuously surrounding edge.

8. The instrument according to claim 1, wherein the hood is movably arranged between a distal and a proximal position.

9. The instrument according to claim 8, wherein the hood is arranged in a translational movable manner.

10. The instrument according to claim 1, wherein the hood is configured in a hollow cylindrical or hollow truncated cone-shaped manner.

11. The instrument according to claim 1, wherein the hood and an extension of the instrument body are arranged only partly extending around the chamber respectively.

12. The instrument according to claim 11, wherein the hood is rotatably supported on the instrument body.

13. The instrument according to claim 1, wherein the instrument body comprises a cleaning window.

14. The instrument according to claim 13, wherein the hood is arranged in a manner covering the cleaning window in its first position and uncovering the cleaning window in its second position.

15. The instrument according to claim 1, wherein the instrument body comprises a second channel.

\* \* \* \* \*